(12) United States Patent
Christenson et al.

(10) Patent No.: US 11,147,918 B2
(45) Date of Patent: Oct. 19, 2021

(54) NEEDLE INSERTION RESPONSIVE SYSTEM

(71) Applicant: Medtronic, Inc., Minneapolis, MN (US)

(72) Inventors: Steven Christenson, Minneapolis, MN (US); Touby Drew, Minneapolis, MN (US); James M. Haase, Minneapolis, MN (US); Scott A. Sarkinen, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 154 days.

(21) Appl. No.: 16/168,358

(22) Filed: Oct. 23, 2018

(65) Prior Publication Data

US 2020/0121850 A1    Apr. 23, 2020

(51) Int. Cl.
*A61M 5/14* (2006.01)
*A61M 5/168* (2006.01)
(Continued)

(52) U.S. Cl.
CPC ...... *A61M 5/16809* (2013.01); *A61M 5/1413* (2013.01); *A61M 5/14276* (2013.01); *A61M 5/162* (2013.01); *A61M 2005/14208* (2013.01); *A61M 2005/1623* (2013.01); *A61M 2205/14* (2013.01); *A61M 2205/18* (2013.01); *A61M 2205/3389* (2013.01); *A61M 2205/3507* (2013.01); *A61M 2205/3523* (2013.01); *A61M 2205/502* (2013.01); *A61M 2205/52* (2013.01);
(Continued)

(58) Field of Classification Search
CPC .................... A61M 5/14276; A61M 2209/045
See application file for complete search history.

(56) References Cited

U.S. PATENT DOCUMENTS 4,360,019 A * 11/1982 Portner ............ A61M 5/14276
604/131
4,573,994 A    3/1986 Fischell et al.
(Continued)

FOREIGN PATENT DOCUMENTS

WO    WO 2013/052414 A2    4/2013

OTHER PUBLICATIONS

Extended European Search Report for European Application No. 19202531.0, dated Jan. 27, 2020.

(Continued)

*Primary Examiner* — William R Carpenter
(74) *Attorney, Agent, or Firm* — Patterson Thuente Pedersen, P.A.

(57) ABSTRACT

A medicament delivery system configured to reduce the risk of inadvertently injecting medicament directly into a patient during a refill procedure via an external refilling apparatus. The medicament delivery system may include an implantable medical pump having a refillable medicament reservoir accessible via an access port, wherein the refillable medicament reservoir includes a flexible diaphragm having a nonlinear spring rate configured to create a relative vacuum within a medicament chamber when medicament is expelled from the medicament chamber beyond a predefined threshold, so as to spontaneously draw a quantity of medicament into the medicament chamber during the refill procedure to reestablish the predefined threshold, thereby confirming proper placement of a portion of the external refilling apparatus into the access port.

20 Claims, 9 Drawing Sheets

(51) Int. Cl.
*A61M 5/162* (2006.01)
*A61M 5/142* (2006.01)

(52) U.S. Cl.
CPC . *A61M 2205/581* (2013.01); *A61M 2205/582* (2013.01); *A61M 2205/8206* (2013.01)

(56) References Cited

U.S. PATENT DOCUMENTS

| | | | |
|---|---|---|---|
| 4,772,263 A * | 9/1988 | Dorman | A61M 5/14276 |
| | | | 128/DIG. 12 |
| 5,217,442 A | 6/1993 | Davis | |
| 6,283,943 B1 | 9/2001 | Dy et al. | |
| 6,579,280 B1 | 6/2003 | Kovach et al. | |
| 6,962,580 B2 | 11/2005 | Adams et al. | |
| 7,072,802 B2 | 7/2006 | Hartlaub | |
| 7,637,897 B2 | 12/2009 | Ginggen | |
| 7,942,863 B2 | 5/2011 | Kalpin et al. | |
| 9,122,785 B2 | 9/2015 | Alme et al. | |
| 9,421,325 B2 * | 8/2016 | Kalpin | A61M 5/14276 |
| 2006/0089619 A1 | 4/2006 | Ginggen | |
| 2006/0089620 A1 * | 4/2006 | Gibson | A61M 5/14586 |
| | | | 604/891.1 |
| 2008/0243093 A1 | 10/2008 | Kalpin et al. | |
| 2011/0301575 A1 | 12/2011 | Miesel et al. | |
| 2012/0053514 A1 | 3/2012 | Robinson et al. | |
| 2013/0116665 A1 | 5/2013 | Humayun et al. | |
| 2014/0228765 A1 | 8/2014 | Burke et al. | |
| 2016/0354540 A1 | 12/2016 | Kalpin | |
| 2017/0043151 A1 | 2/2017 | Bellrichard et al. | |

* cited by examiner

NEEDLE INSERTION RESPONSIVE SYSTEM

TECHNICAL FIELD

The present disclosure relates generally to implantable medical devices, and more particularly to a system and method configured to provide safer refilling of an expandable fluid reservoir thereof with medicament.

BACKGROUND

A variety of medical devices are used for chronic or long-term, delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, pumps or other fluid delivery devices can be used for chronic delivery of therapeutic medicaments, such as drugs or other agents. Typically, such devices provide therapy continuously or periodically according to programmed parameters. The programmed parameters can specify the therapeutic regimen (e.g., the rate, quantity, and timing of medicament delivery to a patient), as well as other functions of the medical device.

Implantable medical infusion pumps have important advantages over other forms of medicament administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood brain barrier adequately if needed in the brain. In addition, infusion of substances from outside the body requires a transcutaneous catheter, which results in other risks such as infection or catheter dislodgment. Further, implantable medical pumps avoid the problem of patient noncompliance, namely the patient failing to take the prescribed drug or therapy as instructed.

Implantable medical infusion pumps are typically implanted at a location within the body of a patient (typically a subcutaneous region in the lower abdomen), and are configured to deliver a fluid medicament through a catheter. The catheter is generally configured as a flexible tube with a lumen running the length of the catheter to a selected delivery site in the body, such as the intracranial or subarachnoid space.

Such implantable medical pumps typically include an expandable fluid reservoir, which is accessible for refill through an access port. During the refill process, it is important that the medicament not be inadvertently injected directly into the body of the patient. If the portion of the refilling apparatus employed to deliver the medicament is not properly positioned within the access port, a potential fatal dose of medicament can be injected directly into a pocket surrounding the implantable pump.

Although various attempts have been made to reduce the likelihood of inadvertent pocket fills during the refill procedure, it is desirous to further enhance safety. Applicants of the present disclosure have developed a system and method to address this concern.

SUMMARY OF THE DISCLOSURE

Embodiments of the present disclosure provide a system and method configured to reduce the risk of inadvertently injecting medicament into a patient during a refill procedure via an external refilling apparatus through the use of an optional flexible diaphragm having a spring rate characteristics configured to create a relative vacuum within a medicament reservoir sufficient to spontaneously draw a quantity of fluid from the external refilling apparatus, an optional needle detection sensor configured to detect the presence of a portion of the refilling apparatus within an access port for the purpose of guiding a user through the procedural steps of the refill procedure, by tying the physical acts associated with the refill procedure to relevant information displayed or configured on a user interface of an external program, or combinations thereof.

One embodiment of the present disclosure provides a medicament delivery system configured to reduce the risk of inadvertently injecting medicament directly into a patient during a refill procedure via an external refilling apparatus. The medicament delivery system can include an implantable medical pump including a refillable medicament reservoir accessible via an access port, wherein the refillable medicament reservoir includes a flexible diaphragm having a nonlinear spring rate configured to create a relative vacuum within a medicament chamber with respect to at least one of an atmospheric pressure, a localized environment in which the implantable medical pump is positioned, or pressure within a vapor chamber at least partially surrounding the medicament chamber when medicament is expelled from the medicament chamber beyond a predefined threshold, so as to spontaneously draw a quantity of medicament into the medicament chamber during the refill procedure to reestablish the predefined threshold, thereby confirming proper placement of a portion of the external refilling apparatus into the access port.

In one embodiment, the flexible diaphragm can include one or more convolutions configured to enable the flexible diaphragm to expand and contract between an extended position and an empty position. In one embodiment, the nonlinear spring rate of the flexible diaphragm can be established via a first biasing element and a second biasing element, wherein the second biasing element has a higher compression spring rate than the compression spring rate of the first biasing element. In one embodiment, the first biasing element and the second biasing element can cooperate to naturally bias the flexible diaphragm towards an expanded position. In one embodiment, as the flexible diaphragm contracts towards an empty position, the nonlinear spring rate of the flexible diaphragm transitions from the compression spring rate of the first biasing element to the higher compression spring rate of the second biasing element. In one embodiment, the first biasing element can include one or more convolutions. In one embodiment, the compression spring rate of the second biasing element can be greater than that of the first biasing element. In one embodiment, the second biasing element can include at least one of: one or more convolutions having a higher compression spring rate than the first biasing element; a wave spring; a convex closed-end of the flexible diaphragm; a concave closed-end of the flexible diaphragm; or a combination thereof.

In one embodiment, the medicament reservoir further includes a vapor chamber configured to apply a substantially constant pressure to an exterior portion of the medicament chamber. In one embodiment, at the predefined threshold, the nonlinear spring rate of the flexible diaphragm reaches a magnitude sufficient to counteract the pressure applied by the vapor chamber. In one embodiment, the predefined threshold is established when approximately up to at one least of 0.25 mL, 0.5 mL, 0.75 mL, 1.0 mL, 1.25 mL, 1.5 mL, 1.75 mL, 2.0 mL, 2.25 mL, 2.5 mL, 2.75 mL, 3.0 mL, 3.25 mL, 3.5 mL, 3.75 mL, or 4.0 mL of medicament remains within the medicament chamber. In one embodiment, further aspiration of medicament from the medicament chamber can establish the relative vacuum within the medicament chamber.

In one embodiment, the medicament delivery system further includes a sensor configured to detect the presence of a portion of the refilling apparatus within the access port. In one embodiment, data gathered by the sensor is logged for future use. In one embodiment, data gathered by the sensor is utilized to prompt a programmer to display user feedback regarding placement of the portion of the refilling apparatus within the access port. In one embodiment data gathered by the sensor is utilized to prompt a programmer to display medicament refill information. In one embodiment the medicament refill information includes at least one of a listing of one or more procedural steps for completing the refill procedure, an instructional video for aid in completing the refill procedure, or a combination thereof.

Another embodiment of the present disclosure provides an implantable medical pump configured to reduce the risk of inadvertently injecting medicament directly into a patient during a refill procedure via an external refilling apparatus. The implantable medical pump can include a medicament reservoir configured to store a quantity of medicament. The medicament reservoir can include a flexible diaphragm defining a medicament chamber. The implantable medical pump can further include an access port configured to provide a pathway for medicament flowing into the medicament reservoir. The flexible diaphragm can have a nonlinear spring rate configured to create a relative vacuum within the medicament chamber when medicament is expelled from the medicament chamber beyond a predefined threshold, so as to spontaneously draw a quantity of medicament into the medicament chamber during the refill procedure to reestablish the predefined threshold, thereby confirming proper placement of a portion of the external refilling apparatus into the access port.

Another embodiment of the present disclosure provides a system and method of reducing the risk of inadvertently injecting medicament directly into a patient during a refill procedure of an implantable medical pump via an external refilling apparatus. The system and method can be configured to: provide an implantable medical pump including a refillable medicament reservoir accessible via an access port, wherein the refillable medicament reservoir includes a flexible diaphragm having a nonlinear spring rate configured to create a relative vacuum within the medicament chamber when medicament is expelled from the medicament chamber beyond a predefined threshold; expel medicament from the medicament chamber beyond a predefined threshold to establish the relative vacuum within the medicament chamber; and insert a portion of the external refilling apparatus into the access port of the implantable medical pump, wherein proper placement of the portion of the external refilling apparatus within the access port is confirmed by a spontaneous draw of a quantity of medicament into the medicament chamber to reestablish the predefined threshold.

Another embodiment of the present disclosure provides a medicament delivery system configured to serve as an aid in guiding a user through the procedural steps of refilling an implantable medical pump with an external refilling apparatus by tying the physical acts associated with a refill procedure to relevant information displayed or configured on a user interface of an external programmer. The implantable medical pump can include a refillable medicament reservoir accessible via an access port having a needle detection sensor configured to detect the presence of a portion of an external refilling apparatus within the access port. The external programmer can be configured to communicate with the implantable medical pump during the refill procedure, wherein sensed data gathered by the needle detection sensor is utilized by the external programmer to prompt the display of information relative to the procedural steps of the refill procedure.

In one embodiment, the absence of sensed data gathered by the needle detection sensor can be utilized by the external programmer to initiate an appropriate workflow, including the steps necessary to initiate a prime bolus. In one embodiment, the sensed data gathered by the needle detection sensor can be utilized by the external programmer to display a reminder for the user to initiate one or more physical process steps of the refill procedure. In one embodiment, the sensed data gathered by the needle detection sensor can be utilized by the external programmer to display user feedback regarding placement of the portion of the external refilling apparatus within the access port. In one embodiment, the sensed data gathered by the needle detection sensor can be utilized by the external programmer to detect an unintentional withdrawal of the portion of the external refilling apparatus from the access port during the refill procedure, thereby providing an advance warning of the increased potential risk of injection of medicament directly into a patient.

In one embodiment, the sensed data gathered by the needle detection sensor can include a timestamp associated with the detection of the presence of a portion of an external refilling apparatus within the access port. In one embodiment, the external programmer can further be configured to determine whether any detected presence of a portion of an external refilling apparatus within the access port was not associated with a refill procedure. In one embodiment, the medicament delivery system can be configured to issue an alert configured to inform a caregiver or user about the possibility of an unauthorized access of the medicament reservoir. In one embodiment, the alert is at least one of an audible signal produced by the implantable medical pump, a message generated by the external programmer, or an electronic message receivable by a remote computing device. In one embodiment, the system further includes a fill sensor configured to determine a volume of medicament within the medicament reservoir.

Another embodiment of the present disclosure provides a system and method of guiding a user through the procedural steps of refilling an implantable medical pump with an external refilling apparatus by tying the physical acts associated with a refill procedure to relevant information displayed or configured on a user interface of an external programmer. The system and method can be configured to provide an implantable medical pump including a refillable medicament reservoir accessible via an access port, wherein the refillable medicament reservoir includes a needle detection sensor configured to detect the presence of a portion of an external refilling apparatus within the access port; and utilize the sensed data gathered by the needle detection sensor to prompt the display of information relevant to the procedural steps of the refill procedure on an external programmer in communication with the implantable medical pump during the refill procedure.

Another embodiment of the present disclosure provides an implantable medical pump configured to serve as an aid to a clinician during a refill procedure by providing one or more auditory or vibratory feedback notifications during the refill procedure. The implantable medical pump can include a refillable medicament reservoir accessible via an access port, and electronics including an alarm and at least one sensor configured to detect a presence of a portion of an external refilling apparatus within the access port, a volume of medicament within the refillable medicament reservoir, or a combination thereof, wherein the electronics can be configured to provide one or more feedback notifications during the refill procedure.

In one embodiment, the one or more feedback notifications can include one of a proper positioning of a needle of a refilling apparatus within the access port, an aspiration of medicament from the refillable medicament reservoir, cessation of an aspiration of medicament from the refillable medicament reservoir, a filling of medicament into the refillable medicament reservoir, cessation of a filling of medicament into the refillable medicament reservoir, removal of a needle of a refilling apparatus from the access port, a state of the refillable medicament reservoir, or a combination thereof. In one embodiment, the electronics can be configured to accept input from an external programmer to establish a predefined window of time to initiate a programmer-less refill procedure. In one embodiment, the at least one sensor can be configured to detect the initiation of a refill procedure during the predefined window of time. In one embodiment, the electronics can be configured to issue an alert if the at least one sensor detects the insertion of a needle into the access port prior to the predefined window of time.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
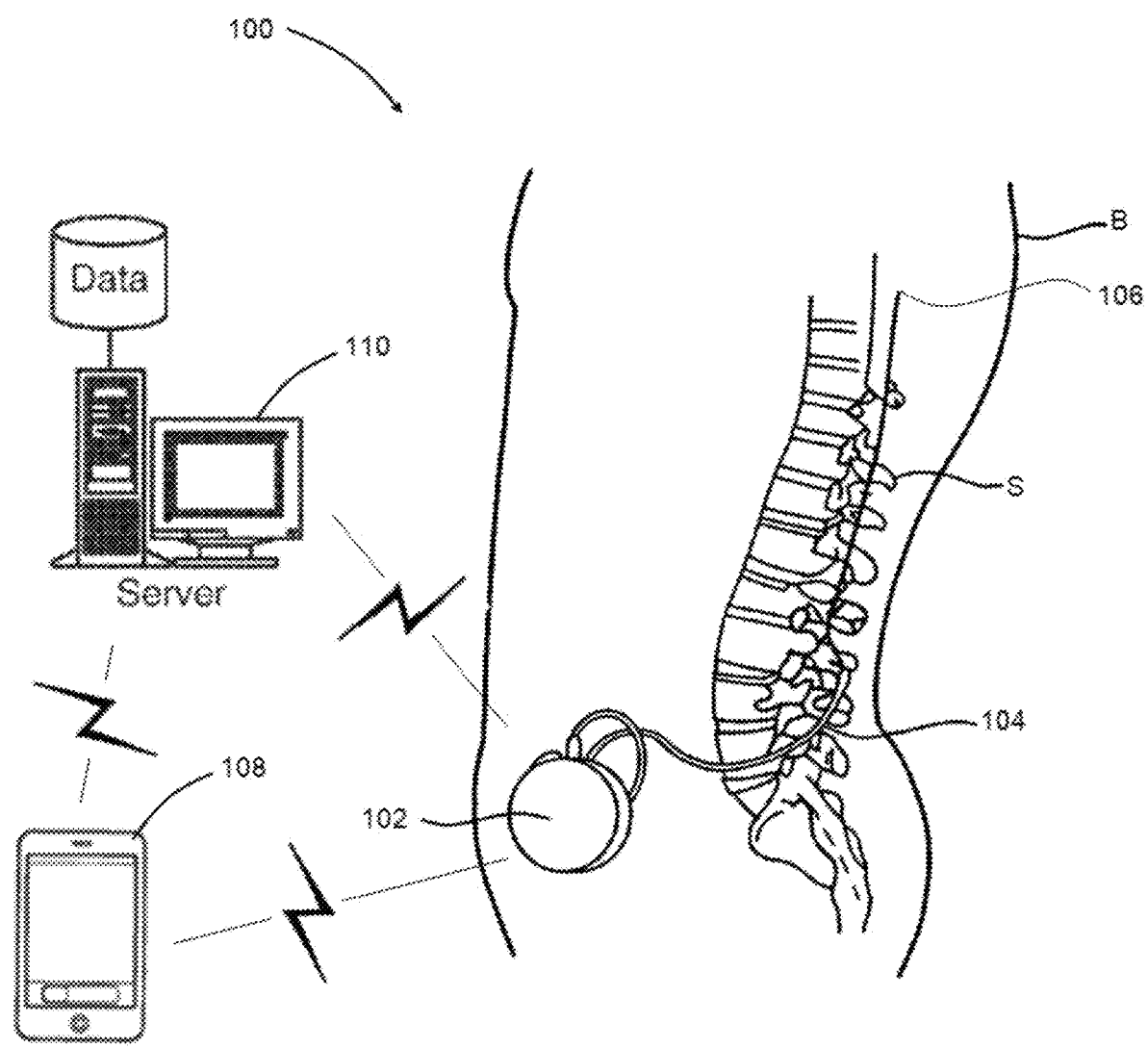
FIG. 1 is a schematic view depicting medicament delivery system in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a schematic view of a medicament delivery system 100 is depicted in accordance with an embodiment of the disclosure. The medicament delivery system 100 can include an implantable medical pump 102 and a catheter 104. As depicted, the implantable medical pump 102 can be implanted within the body B of a patient. The implantable medical pump 102 can be in fluid communication with the catheter 104 having a distal tip 106 positioned within, for example, the subarachnoid space of the patient's spinal column S, thereby enabling intrathecal delivery of medicament through a lumen of the catheter 104. In other embodiments, the distal tip 106 can be positioned within the intracranial space, or other areas within the patient for targeted delivery of medicament. In one embodiment, the medical delivery system can further include an optional external programmer 108 and an optional server 110 configured to communicate with the implantable medical pump 102, and with one another.

Figure 2A:
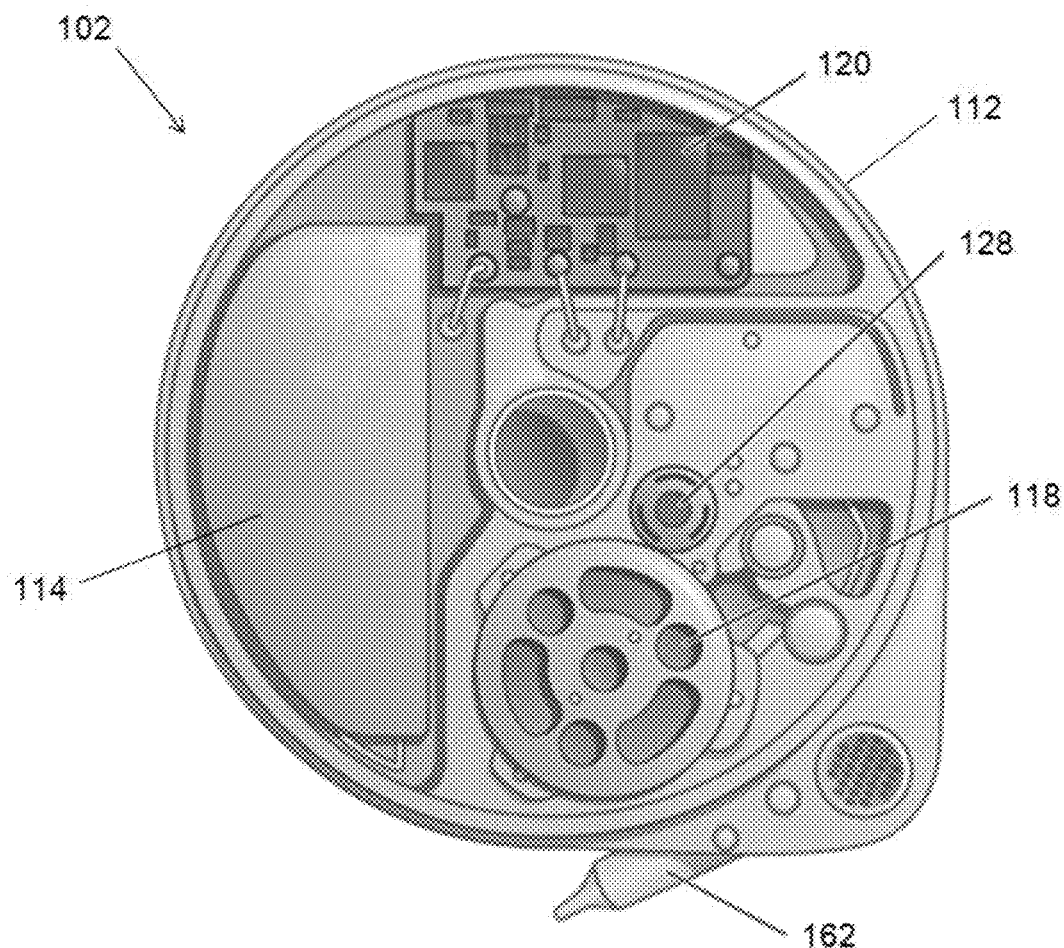
FIG. 2A is a cross-sectional plan view depicting an implantable medical pump in accordance with an embodiment of the disclosure.

Referring to FIG. 2A, a cross-sectional plan view of an implantable medical pump 102 is depicted in accordance with an embodiment of the disclosure. Implantable medical pump 102 can generally include a housing 112, power source 114, medicament reservoir 116, medicament pump 118, and electronics 120. The housing 112 can be constructed of a material that is biocompatible and hermetically sealed, such as titanium, tantalum, stainless steel, plastic, ceramic, or the like.

Figure 3:
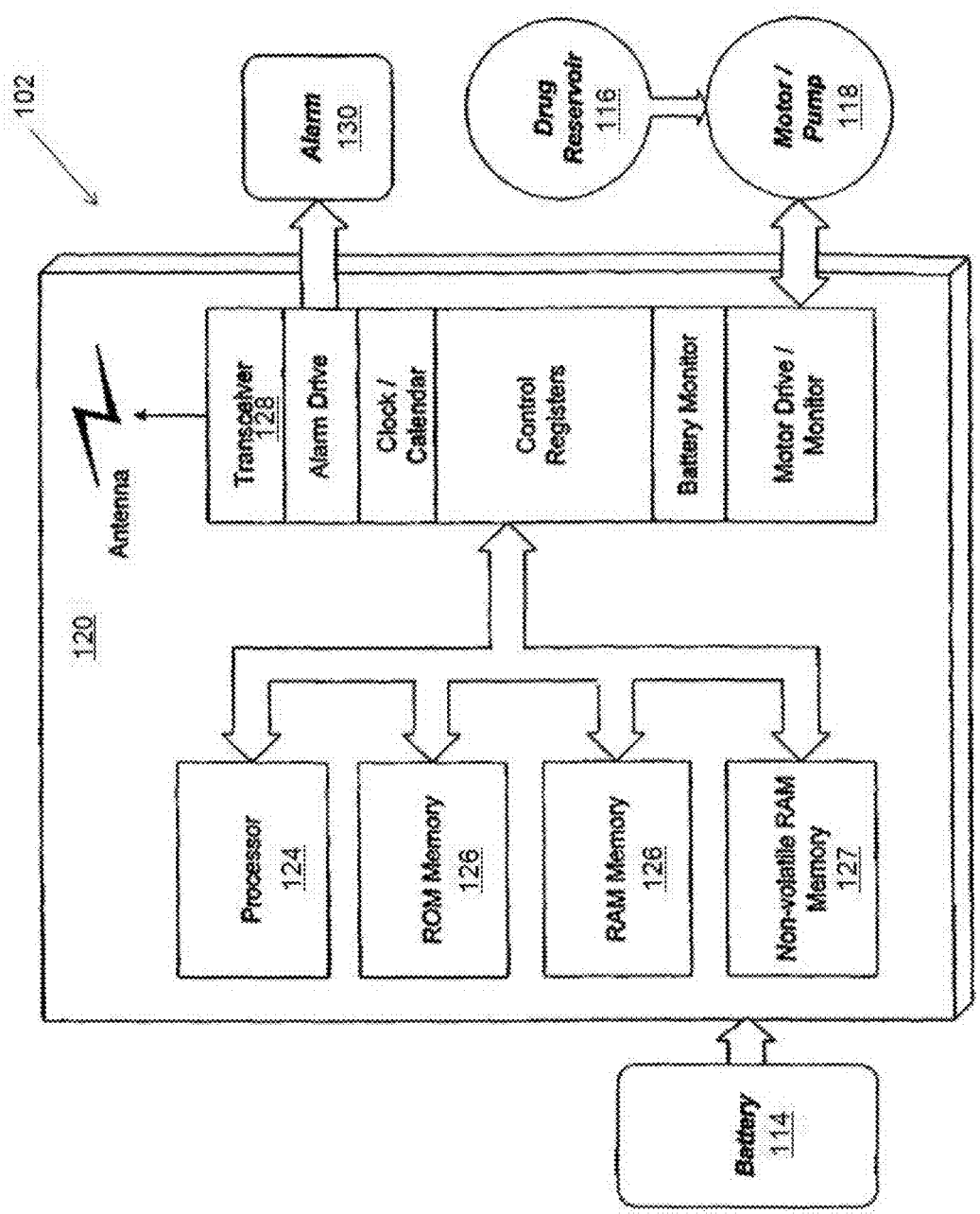
FIG. 3 is a block diagram depicting an implantable medical pump in accordance with an embodiment of the disclosure.
Figure 4A:
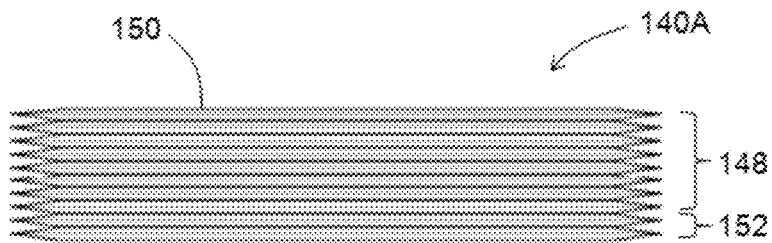
FIG. 4A depicts a second embodiment of a flexible diaphragm in accordance with the disclosure.
Figure 4B:
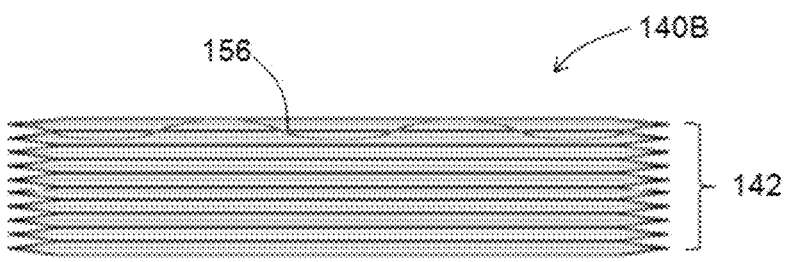
FIG. 4B depicts a third embodiment of a flexible diaphragm in accordance with the disclosure.
Figure 4C:
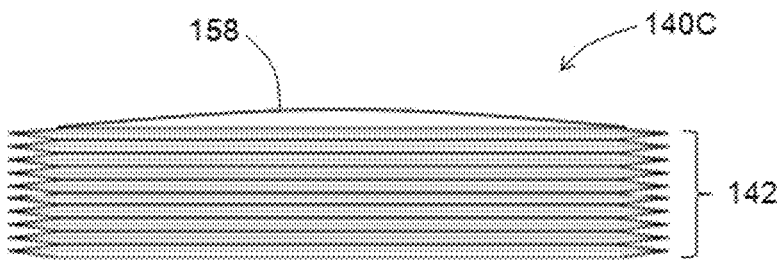
FIG. 4C depicts a fourth embodiment of a flexible diaphragm in accordance with the disclosure.
Figure 4D:
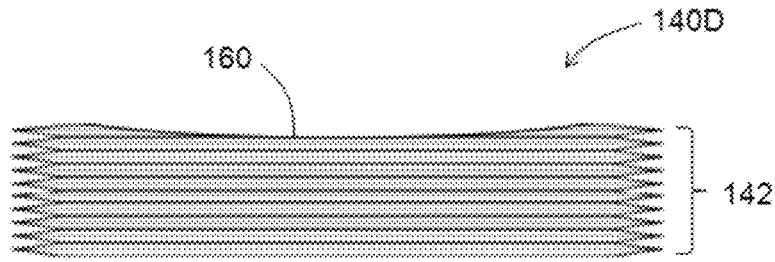
FIG. 4D depicts a fifth embodiment of a flexible diaphragm in accordance with the disclosure.

Referring to FIG. 3, a block diagram of an implantable medical pump 102 is depicted in accordance with an embodiment of the disclosure. The electronics 120 can be carried in the housing 112, and can be in electrical communication with the medicament pump 118 and power source 114. The power source 114 can be a battery, such as a lithium-ion battery. The power source 114 can be carried in the housing 112, and can be selected to operate the medicament pump 118 and electronics 120.

The electronics 120 can include a processor 124, memory 126/127, and transceiver circuitry 128. In one embodiment, the processor 124 can be an Application-Specific Integrated Circuit (ASIC) state machine, gate array, controller, or the like. The electronics 120 can be generally configured to control infusion of medicament according to programmed parameters or a specified treatment protocol. The programmed parameters or specified treatment protocol can be stored in the memory 126. The transceiver circuitry 128 can be configured to receive information from and transmit information to the external programmer 108 and server 110. In one embodiment, the electronics 120 can be further be configured to operate a number of other features, such a patient alarm 130.

The implantable medical pump 102 can be configured to receive programmed parameters and other updates from the external programmer 108, which can communicate with the implantable medical pump 102 through well-known techniques such as wireless telemetry. In some embodiments, the external programmer 108 can be configured for exclusive communication with one or more implantable medical pumps 102. In other embodiments, the external programmer 108 can be any computing platform, such as a mobile phone or tablet. In some embodiments, the implantable medical pump 102 and external programmer 108 can further be in communication with a cloud-based server 110. The server 110 can be configured to receive, store and transmit information, such as program parameters, treatment protocols, drug libraries, and patient information, as well as to receive and store data recorded by the implantable medical pump 102.

Figure 2B:
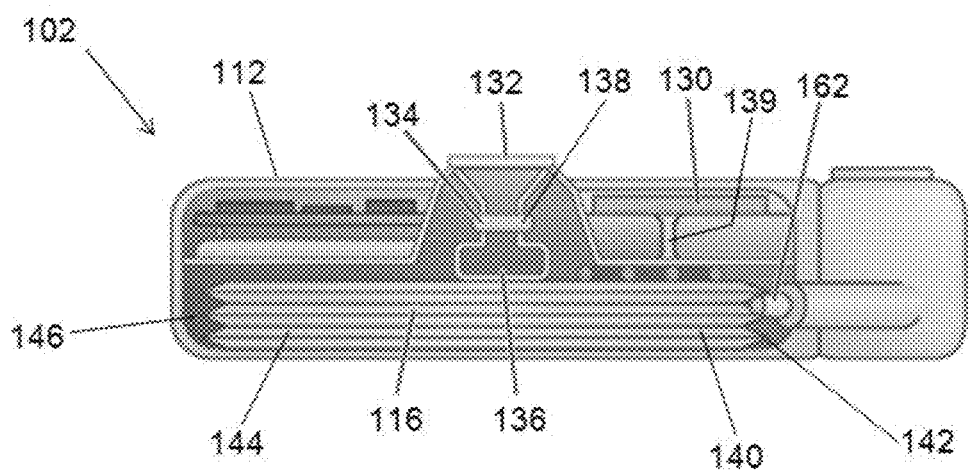
FIG. 2B is a cross-sectional profile view depicting the implantable medical pump of FIG. 2A.

Referring to FIG. 2B, a cross-sectional profile view of an implantable medical pump is depicted in accordance with an embodiment of the disclosure. The medicament reservoir 116 can be carried by the housing 112 and can be configured to contain medicament. In one embodiment, medicament within the medicament reservoir 116 can be accessed via an access port 132. Accordingly, the access port 132 can be utilized to refill, empty, or exchange the fluid within the medicament reservoir 116. In one embodiment, the access port 132 can include a self-sealing septum 134 and a needle stop 136. The self-sealing septum 134 can be constructed of a silicone rubber or other material having desirable self-sealing and longevity characteristics. In one embodiment, the access port 132 can further include an optional needle detection sensor 138, for example in the form of a mechanical switch or capacitive probe, configured to detect the presence of an injection needle of a refilling apparatus.

The medicament reservoir 116 can include a flexible diaphragm 140. The flexible diaphragm 140, alternatively referred to as a bellows, can be substantially cylindrical in shape and can include one or more convolutions 142 configured to enable the flexible diaphragm 140 to expand and contract between an extended or full position and an empty position. In one embodiment, the flexible diaphragm 140 can divide the medicament reservoir 116 into a medicament chamber 144 containing liquid medicament (within the flexible diaphragm 140), and a vapor chamber 146 (surrounding the flexible diaphragm 140)

The vapor chamber 146 surrounding the medicament chamber 144 can be configured to be filled with a fluorocarbon, such as Freon® 113 or other appropriate propellant, in a saturated vapor and liquid form. Over normal internal body temperatures, Freon 113 has a substantially linear pressure characteristic as it changes from liquid to vapor and vice versa. Therefore, at an essentially constant temperature within the human body (e.g., approximately 98.6° F.), the propellant within the vapor chamber 146 maintains substantially fixed pressure of around 19 psia (around +4.3 psig) regardless of the amount of medicament disposed within the medicament chamber 144.

As the medicament chamber 144 is filled with medicament, as hereinafter described, the flexible diaphragm 140 extends downwardly (with reference to FIG. 2B) toward a bottom portion of the housing 112 until it has reached a desired degree of fullness. In one embodiment, the flexible diaphragm 140 can have a compression spring rate which tends to naturally bias the flexible diaphragm 140 towards an expanded position. In particular, over the approximately 0.5 inch travel of the flexible diaphragm 140 between the expanded position and the empty position, the convolutions 142 can provide a linear compression spring rate configured to generally act against (but not completely counteract) the pressure within the vapor chamber 146.

In one embodiment, the implantable medical pump 102 can optionally include a fill sensor 139, for example in the form of an infrared (IR) transducer or other sensor configured to detect the expansion/contraction of the flexible diaphragm 140. Accordingly, the fill sensor 139 can be utilized to measure a dimension of the medicament reservoir 116 for the purpose of determining the volume of medicament therewithin.

Referring to FIGS. 4A-D, alternative embodiments of flexible diaphragms 140A-D are depicted in accordance with the disclosure. In a second embodiment (depicted in FIG.4A), a first set of convolutions 148 (e.g., a first biasing element) positioned in proximity to a first end 150 of the flexible diaphragm 140A can be configured to have a relatively lower compression spring rate than a second set of convolutions 152 (e.g., a second biasing element) positioned in proximity to a second end 154 of the flexible diaphragm 140A. As depicted, the first set 148 can include eight convolutions and the second set 152 can include two convolutions; although sets including other quantities of convolutions, including a single convolution, are contemplated. For example, the flexible diaphragm 140A can include a total of between about two and about twenty convolutions, wherein a quantity of the convolutions make up the first set 148 of convolutions and the remainder the convolutions make up a second set 152 of convolutions. In one embodiment, the first set of convolutions 148 can have a spring rate between about 6 lb/inch and about 20 lb/inch, and the second set of convolutions 152 can have a spring rate greater than about 20 lb/inch; thus, the second set of convolutions 152 can have a higher compression spring rate than the compression spring rate of the first set of convolutions 148.

Accordingly, as the flexible diaphragm 140A collapses, the first set of convolutions 148 are compressed towards each other at a faster rate than the second set of convolutions 152. As the flexible diaphragm 140A further transitions towards the empty position, the first set of convolutions 148 begin to contact each other, and the compression spring rate of the diaphragm 140A transitions from between around 8-17 lb/inch to around 30 lb/inch, to eventually reach a compression spring rate sufficient to counteract and optionally exceed to the pressure within the medicament chamber 144. In one embodiment, a compression spring rate equal and opposite to the pressure within the medicament chamber 144 can be established when approximately up to at one least of 0.25 mL, 0.5 mL, 0.75 mL, 1.0 mL, 1.25 mL, 1.5 mL, 1.75 mL, 2.0 mL, 2.25 mL, 2.5 mL, 2.75 mL, 3.0 mL, 3.25 mL, 3.5 mL, 3.75 mL, or 4.0 mL of medicament remains within the medicament chamber 144; although other quantities of remaining medicament are also contemplated. Further aspiration of the remaining medicament from the medicament chamber 144 via the medicament pump 118 can cause the compression spring rate of the flexible diaphragm 140A to further increase, thereby creating a relative vacuum within the medicament chamber 144 with respect to at least one of an atmospheric pressure, a localized environment in which the implantable medical pump 102 is positioned, or pressure within a vapor chamber 146 at least partially surrounding the medicament chamber 144.

In a third embodiment (depicted in FIG. 4B), the flexible diaphragm 140B can include a wave spring 156 configured to increase the compression spring rate as the flexible diaphragm 140B is compressed or collapsed. That is, in addition to convolutions 142 having a spring rate between about 6 lb/inch and about 20 lb/inch (e.g., a first biasing element), the flexible diaphragm 140B can include a wave spring 156 (e.g., a second biasing element) having an additional compression spring rate (e.g., up to about 15 lb/inch) to supplement the compressive spring rate of the convolutions 142. The wave spring 156 can be positioned at one end of the flexible diaphragm 140B. Upon compression of the flexible diaphragm 140B towards the empty position, the wave spring 156 can be configured to cause a sudden increase in compression spring rate when the medicament remaining in the medicament chamber 144 reaches a predefined threshold. In one embodiment, the predefined threshold can be established when a predefined quantity of medicament remains within the medicament chamber.

In a fourth embodiment (depicted in FIG. 4C), the flexible diaphragm 140C can include a convex closed-end 158 configured to increase the compression spring rate as the flexible diaphragm 140C is compressed or collapsed. That is, in addition to the convolutions 142 having a first spring rate (e.g., a first biasing element), the flexible diaphragm 140C can include a convex closed-end 158 (e.g., a second biasing element) having a relatively higher compression spring rate than the compression spring rate of the convolutions 142. Accordingly, as the flexible diaphragm 140C collapses towards the empty position, the convolutions 142 begin to contact each other, and the compression spring rate of the diaphragm 140C can transition from the first spring rate to a second spring rate, to eventually reach a compression spring rate sufficient to counteract and optionally exceed the pressure within the medicament chamber 144. In one embodiment, a compression spring rate equal and opposite to the pressure within the medicament chamber 144 can be established when the remaining medicament in the medicament chamber 144 reaches a predefined threshold. Further aspiration of the remaining medicament from the medicament chamber 144 can create a relative vacuum within the medicament chamber 144.

In a fifth embodiment (depicted in FIG. 4D), the flexible diaphragm 140 can include a concave closed-end 160 (e.g., a second biasing element) configured to increase the compression spring rate as the flexible diaphragm 140D is compressed or collapsed. Similar to the third embodiment, as the flexible diaphragm 140C collapses, the convolutions 142 (e.g., the first biasing element) begin to contact each other, and the compression spring rate of the diaphragm 140C transitions from a first spring rate, to eventually reach a compression spring rate sufficient to counteract and optionally exceed the pressure within the medicament chamber 144. Further aspiration of the remaining medicament from the medicament chamber 144 can create a relative vacuum within the medicament chamber 144 relative to at least one of the atmospheric pressure or pressure within the vapor chamber 146.

The flexible diaphragms depicted in FIGS. 4A-D are merely example embodiments. It should be understood that the various features of the flexible diaphragm embodiments can be combined to produce additional or hybrid embodiments.

Figure 5B:
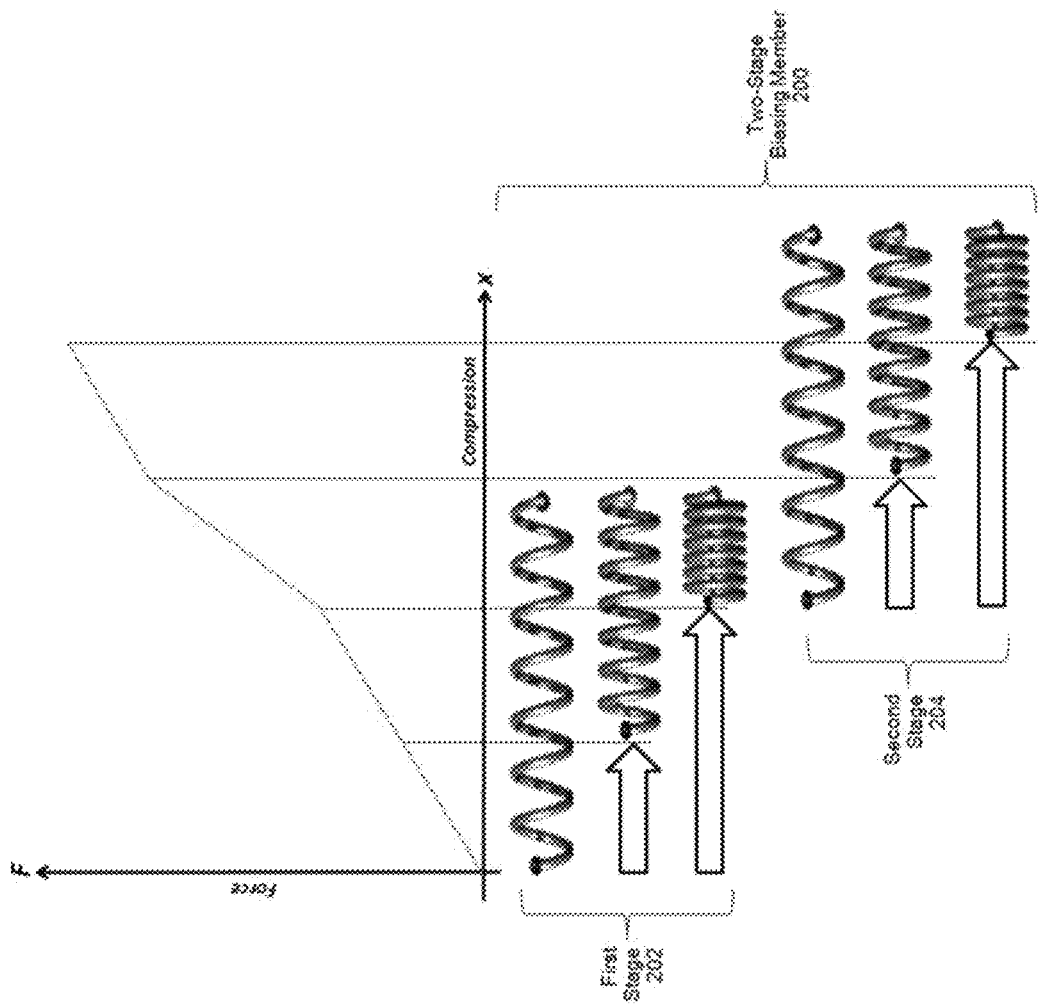
FIG. 5B a graphical representation of an applied force versus a compression distance of a two-stage biasing element is depicted in accordance with an embodiment of the disclosure.
Figure 5A:
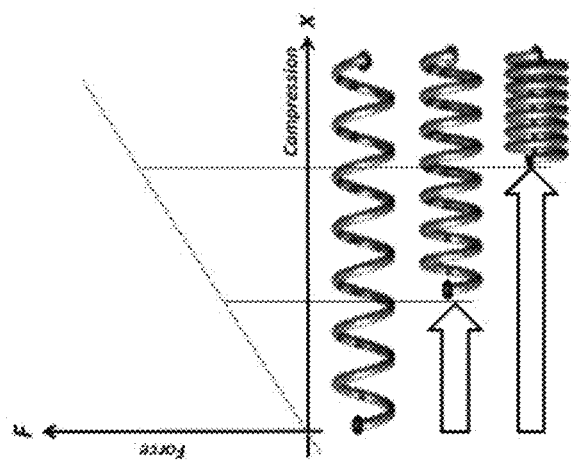
FIG. 5A a graphical representation of an applied force versus a compression distance of a single-stage biasing element is depicted in accordance with an embodiment of the disclosure.

Referring to FIG. 5A, a graphical representation of an applied force versus a compression distance of a single-stage biasing element is depicted in accordance with an embodiment of the disclosure. The force (F) required to compress a biasing element a given distance can be determined according to Hooke's law:

$$F=kx$$

wherein k is a constant factor characteristic of the spring (e.g. its stiffness), and x is the compression distance. For example, with a spring constant (k) of approximately 10 lb/inch, the force (F) required to compress the biasing element the distances (x) of 0.25 inches and 0.5 inches, equals approximately 2.5 lbs and 5 lbs respectively.

Referring to FIG. 5B, a graphical representation of an applied force versus a compression distance of a two-stage biasing element 200 is depicted in accordance with an embodiment of the disclosure. In one embodiment, the first stage biasing element 202 can be configured to compress over a distance of 0.375 inches. Accordingly, the force required to compress the biasing element between 0-0.25 inches increases linearly. For example, with a spring constant (k) of approximately 10 lb/inch, the force (F) required to compress the first stage biasing element 202 a distance (x) of 0.25 inches equals approximately 2.5 lbs.

The second stage biasing element 204 can be configured to compress over a similar distance; however, the two-stage biasing element can be configured such that compression does not begin until approximately 0.25 inches. Accordingly, as the second stage biasing element 204 begins to compress, the force (F) required to compress both the first stage biasing element 202 and the second stage biasing element 204 are summed. For example, if both the first and second stage biasing elements have a spring constant (k) of approximately 10 lb/inch, the force (F) required to compress the two-stage biasing element to a distance (x) of 0.375 inches equals approximately 5 lbs (3.75 lbs for the first stage 202 and 1.25 lbs for the second stage 204). Thus, the spring rate of the two-stage biasing element can abruptly change at the distance where the second stage biasing element 204 begins to compress.

In one embodiment, the first stage biasing element 202 can be fully compressed at approximately 0.375 inches. Accordingly, at a distance of 0.5 inches, the force (F) required to compress the two-stage biasing element equals approximately 6.5 lbs (3.75 lbs for the first stage 202 and 2.5 lbs for the second stage 204). Other compression distances (x) and spring constants (k) of the first stage 202 and the second stage 204 biasing elements are also contemplated. The inclusion of additional stages is also contemplated.

Accordingly, the biasing element 200 can be configured to create an abrupt change in the spring rate over a given compression distance. In one embodiment, the biasing element 200 can be configured to transition from a first spring rate to a second spring rate, wherein the second spring rate is greater than the first spring rate. In one embodiment, the biasing element can further be configured to transition from the second spring rate to a third spring rate, wherein the third spring rate is greater than the second spring rate.

With continued reference to FIGS. 2A-B, the medicament pump 118 can be carried by the housing 112. The medicament pump 118 can be in fluid communication with the medicament reservoir 116 and can be in electrical communication with the electronics 120. The medicament pump 118 can be any pump sufficient for infusing medicament to the patient, such as a peristaltic pump, piston pump, a pump powered by a stepper motor, a pump powered by an AC motor, a pump powered by a DC motor, an electrostatic diaphragm, a piezioelectric motor, a solenoid, a shape memory alloy, or the like.

The catheter 104 can be operably coupled to the implantable medical pump 102 via catheter port 162, such that the lumen of the catheter 104 is in fluid communication with the medical pump 118 and reservoir 116. The distal tip 106 of the catheter 104 can be positioned in the subarachnoid space, intracranial space, or other areas within a patient, for targeted delivery of medicament.

Figure 6:
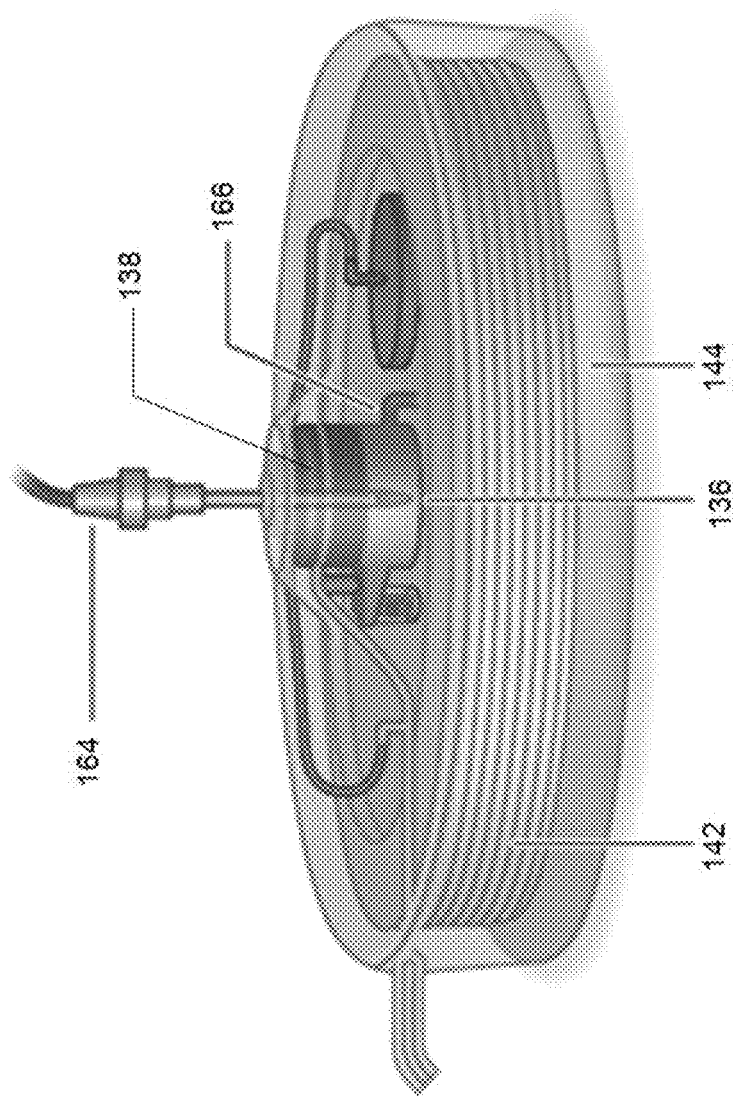
FIG. 6 depicts an implantable medical pump engaged in a medicament refilling procedure, in accordance with an embodiment of the disclosure.

Referring to FIG. 6, an implantable medical pump 102 engaged in a medicament refilling procedure is depicted in accordance with an embodiment of the disclosure. During the refill procedure, the access port 132 of the implantable medical pump 102 is located, and a portion of a refilling apparatus 164 is inserted therein. For example, a distal tip of a needle of the refilling apparatus 164 can pierce the self-sealing septum 134, thereby establishing fluid communication between the refilling apparatus 164 and the refill path 166 of the implantable medical pump 102. The needle stop 136 inhibits further distal movement of the distal tip of the refilling apparatus 164 within the access port 132.

In one embodiment, at least one of the needle detection sensor 138 and fill sensor 139, which can optionally be in communication with the electronics 120, can be configured to detect or sense the placement of the needle within the access port 132 and flow of medicament into and out of the medicament reservoir 116 for the purpose of providing feedback to a clinician (e.g., an audible tone or vibratory response) during the refill procedure. For example, in one embodiment, the needle detection sensor 138 can be configured to detect proper placement or positioning of the needle. An audible tone or vibratory response, for example, by alarm 130 within the implantable medical pump 102 can be produced to notify the clinician of proper placement or positioning of the needle. Thereafter, an audible tone or vibratory response can be produced to notify the clinician of removal of the needle from the access port 132, including an inadvertent removal of the needle. Similarly, audible tones or vibratory responses can be produced to notify the clinician that aspiration of the medicament reservoir 116 has started or has ceased (as detected by the fill sensor 139), that the medicament reservoir 116 has reached an empty state, that filling of the medicament reservoir 116 has started or ceased (as detected by the fill sensor 139), or that the medicament reservoir 116 has reached a full state.

Figure 7:
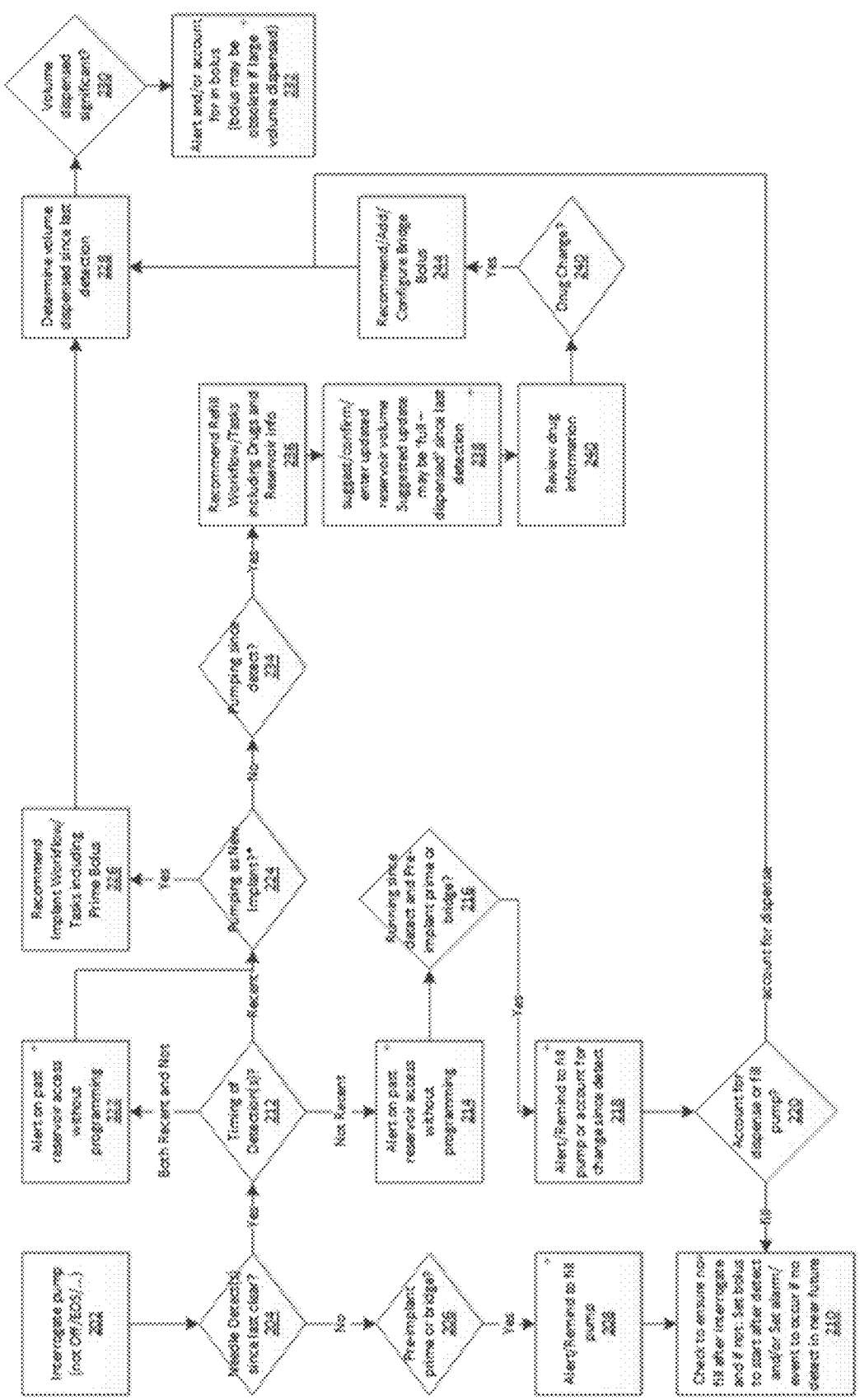
FIG. 7 depicts a flowchart modeling the utilization of a needle detection sensor to trigger one or more automated system responses in accordance with an embodiment of the disclosure.

In one embodiment, the needle detection sensor 138 can be utilized to log the date and time of placement of a needle within the access port 132 for use in providing user feedback, for example, via the external programmer 108 or server 110. Some embodiments of the present disclosure can be configured to serve as an aid in aligning a timing between physical actions taken during a refill procedure and one or more corresponding virtual steps performed in conjunction with the external programmer 108, for example by utilizing a needle detection sensor 138 or fill sensor 139 to trigger one or more automated responses within either the implantable medical pump 102 itself or within the external programmer 108. Conversely, virtual steps completed by the system 100 (e.g., user interaction with the external programmer 108) can be configured to change expectations and behavior of the system 100 with regard to anticipated physical steps of the refill procedure. Referring to FIG. 7, a flowchart modeling the utilization of the needle detection sensor 138 to trigger one or more automated responses is depicted in accordance with an embodiment of the disclosure.

At 202, the external programmer 108 can interrogate the implantable medical pump 102, thereby establishing communication between the pump 102 and the programmer 108, either directly or via server 110. At 204, data from the needle detection sensor 138 can be communicated to the external programmer 108 for the determination of if and when a needle was last detected within the access port 132. If no needle has been detected since the last medicament refilling procedure, at 206, the external programmer 108 can present an inquiry, for example via a user interface, as to whether the programming of a pre-implant prime or a bridge between an old medicament and a new medicament is required. At 208, the external programmer 108 can present a reminder for the user to initiate the physical process of the refilling procedure. In some embodiments, the external programmer 108 can display related refill information, accuracy information, drug information, etc. The related drug refill information can include the listing of procedural steps and one or more instructional videos for aid in completing the refill procedure according to recommended guidelines. In some embodiments, one or more of the procedural steps can be delayed to account for a natural workflow during the procedure.

In one embodiment, the data gathered by the needle detection sensor 138 can be utilized to prompt the programmer 108 to display user feedback regarding placement of the portion of the refilling apparatus 164 within the access port 132. For example, in one embodiment, the needle detection sensor 138 can be configured to sense an ideal placement of the refilling apparatus 164, and prompt the user to reposition the refilling apparatus 164 if a less than ideal placement of the refilling apparatus 164 is sensed. Accordingly, in one embodiment, the needle detection sensor 138 can be utilized to detect an accidental or unintentional withdrawal of the needle from the access port 132 during the refill procedure, thereby providing an advance warning of the increased potential risk of injecting medicament directly into the patient.

At 210, the external programmer 108 can be configured to program the pump 102 to either initiate medicament delivery after a needle has been detected by the needle detection sensor 138, or to activate alarm 134 or provide another notification, if no needle has been detected by the needle detection sensor 138 within a predefined period of time. Accordingly, in one embodiment, the medicament delivery system 100 is configured to correlate the initiation of a refill procedure with an expected refill window.

Referring back to 204, if a needle has been detected by the needle detection sensor 138 since the last medical refilling procedure, at 212, a determination of when the needle was detected can be made. If the needle detection was not recent, for example the needle detection occurred before initiation of the medicament refilling procedure or programming session, at 214, the external programmer 108 can issue an alert configured to inform a caregiver or user about the possibility of an unauthorized access of the medicament reservoir 116. In embodiments, the alert can be generated at the pump 102 via the alarm 130, displayed on a user interface of the external programmer 108, or appear as an email, text, or other instant electronic message generated by the server 110 and sent to a mobile computing device.

At 216, the external programmer 108 can present an inquiry as to whether the pump 102 has been operating since the last needle detection, which can be useful in accounting for any deviation in actual medicament quantity from an expected medicament quantity. At 216, the external programmer 108 can further present an inquiry as to whether programming of a pre-implant prime or bridge is required. At 218, the external programmer 108 can present a reminder for the user to initiate the physical process of the refilling procedure. At 220, the external programmer 108 can provide an accounting for any deviation in medicament quantity since the last needle detection for use during the refill procedure.

Referring back to 212, if the needle detection sensor 138 has detected a needle both recently as well as at a previous time not in connection with a known refill procedure, at 222, the external programmer 108 can issue an alert configured to inform the caregiver or user about the possibility of an unauthorized access at the medicament reservoir 116. Conversely, if the needle detection was recent (e.g., in connection with an ongoing medicament refilling procedure programming session), at 224, the external programmer 108 can determine as to whether the pump 102 is a new implant. If the pump 102 is a new implant, at 226, the external programmer 108 can initiate an appropriate, for example the typical new implant workflow, which can include a plurality of tasks including the steps necessary to initiate a prime bolus.

At 228, the external programmer 108 can estimate the volume of medicament dispensed since the last reservoir 116 fill or refill procedure. At 230, the external programmer 108 can determine whether the volume or quantity of medicament dispensed since the last fill or refill procedure is significant (e.g., whether the patient could potentially be harmed by not accounting for the field drugged and is already in the fluid pathway from the reservoir 116 to the patient). If it is determined that the volume of medicament dispensed since the last fill or refill procedure is significant, at 232, the external programmer 108 can issue an alert. In one embodiment, at 232, the external programmer can provide an accounting for the quantity of medicament dispensed since the last fill or refill procedure.

Referring back to 224, if it is determined that the pump 102 is not a new implant, at 234, a determination can be made as to whether the pump 102 has been operating since the last needle detection, which can be useful in determining whether it is necessary to account for a potential discrepancy in medicament volume within the reservoir 116. At 236, the external programmer 108 can initiate the typical refill workflow, which can include a plurality of tasks including drug and reservoir information. At 238, the external programmer 108 can account for a dispensed quantity of medicament since the last needle detection or refill procedure. At 240, the external programmer 108 can display related drug information, etc.

At 242, an inquiry can be made as to whether a change in medicament is desired. If a change in medicament is to be made, at 244, the external programmer can recommend or initiate the procedures for a bridge bolus, to create a bridge between the old medicament and the new medicament to account for any differences in drug concentrations, etc.

Figure 8:
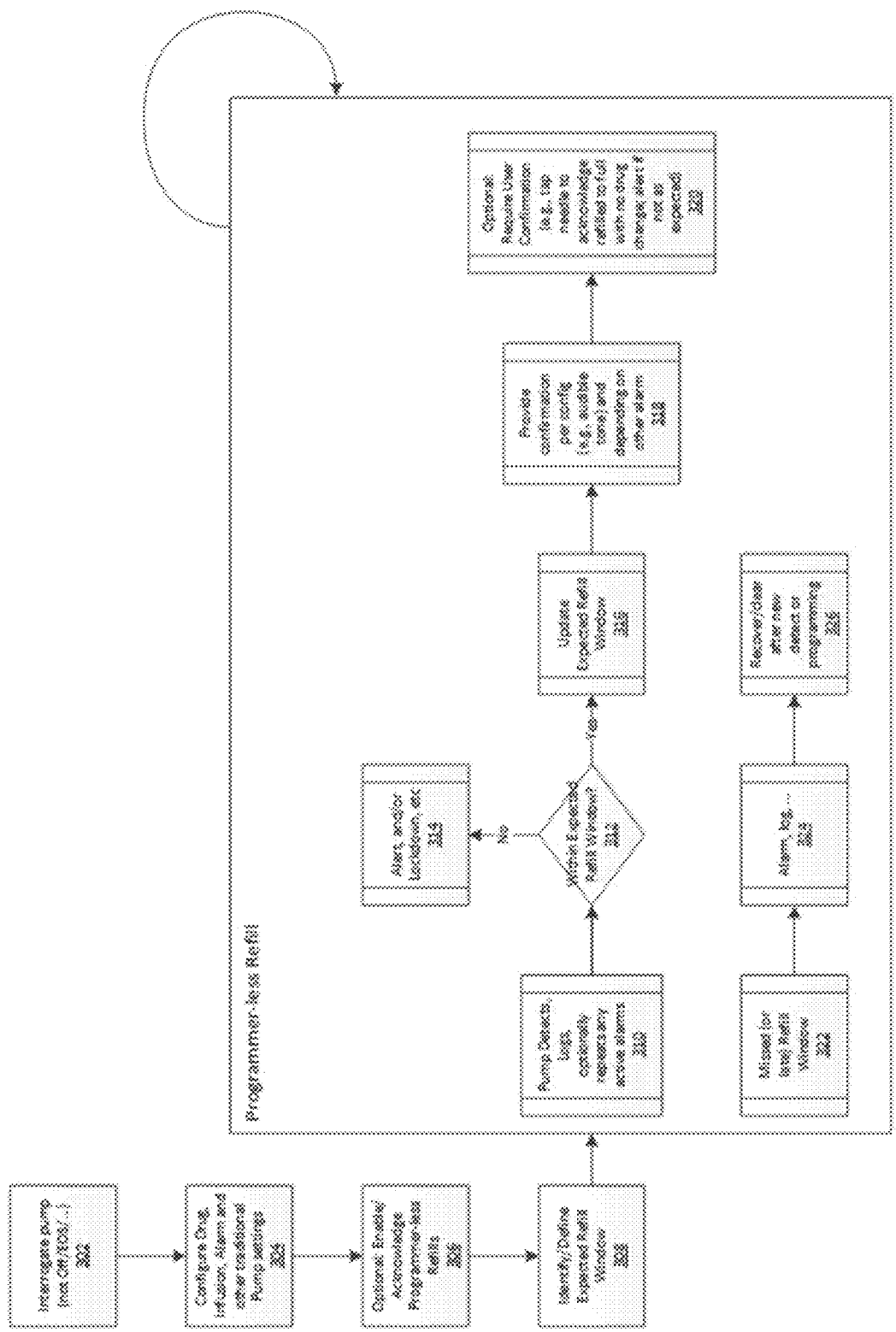
FIG. 8 depicts a flowchart modeling a programmer-less refill procedure in accordance with an embodiment of the disclosure.

Some embodiments of the present disclosure can be configured to address the desire to perform the refill procedure remotely from an external programmer, by configuring the pump 102 to accept a medicament refill and step a user through the refill procedure in the absence of an external programmer 108. Referring to FIG. 8, a flowchart modeling a programmer-less refill procedure is depicted in accordance with an embodiment of the disclosure.

At 302, the external programmer 108 can interrogate the implantable medical pump 102, thereby establishing communication between the pump 102 and programmer 108, either directly or via server 110. At 304, the external programmer 108 can inquire as to whether it is desired to configure or update the pump settings. At 306, a caregiver or user can enable, select or acknowledge a programmer-less refill option, thereby configuring the pump 102 to accept a medicament refill within a predefined window of time (alternatively referred to as a refill window). At 308, the refill window during which the refill procedure is to be initiated can be established. In some embodiments, multiple refill windows can be defined, thereby enabling multiple programmer-less refills. Thereafter, communications between the pump 102 and the programmer 108 can be concluded.

At 310, the needle detection sensor 138 can be configured to detect or sense the insertion of a needle into the access port 132. At 312, a determination can be made by the pump 102 as to whether the insertion of the needle into the access port 132 occurred during the refill window. If the insertion of the needle into the access port 132 is sensed prior to the refill window, at 314, the pump 102 can issue an alert configured to inform a caregiver or user about the possibility of an unauthorized access of the medicament reservoir 116. Alternatively, if the insertion of the needle into the access port 132 is sensed during the refill window, at 316, the initiation of refill procedures can be confirmed and the refill window can be closed. Thereafter, the medicament reservoir 116 can be refilled with medicament.

Upon the medicament reservoir 116 reaching a predefined refill level, at 318, the pump 102 can provide a confirmation (e.g., an audible tone or haptic feedback via alarm 130) that a predefined quantity of medicament has been deposited into the medicament reservoir 116. At 320, a caregiver or user can provide a confirmation that the refill procedure is complete or nearing completion. For example, in one embodiment, an external force sensed by an accelerometer, such as a tap by a user, can serve as the confirmation. In other embodiments, the positioning of a key fob or magnet in proximity to the pump 102 can serve as the confirmation. In one embodiment, the confirmation can be completed prior to removal of the needle from the access port 132, such that a sensing of a removal of the needle by the needle detection sensor 138 is expected, and not interpreted as an accidental or unintentional withdrawal of the needle from the access port 132. In one embodiment, the pump 102 can further request a confirmation that the medicament has not changed.

In one embodiment, different audible tones produced by the pump 102 can signal different conditions experienced by the pump 102 throughout the refill process. For example, proper insertion of a needle into the access port 132 can be signaled by a first audible tone, injection of medicament into the reservoir 116 can be signaled by a second audible tone, a full reservoir status can be signaled by a third audible tone, and removal of the needle from the access port 132 and completion of the refill procedure can be signaled by a fourth audible tone. Other audible tones signaling other pump 102 conditions, such as over-pressurization of the reservoir 116 are also contemplated.

Alternatively, if needle detection sensor 138 fails to detect or sense the insertion of the needle into the access port prior to the completion of the refill window, at 322 the failure to initiate refill procedures can be confirmed and the refill window can be closed. At 324, the pump 102 can initiate an alarm (e.g., an audible tone via alarm 130) configured to inform a caregiver or user about the failure to initiate refill procedures within the refill window. At 326, the alarm can be acknowledged via a predefined confirmation code or with the external programmer 108.

Figure 9:
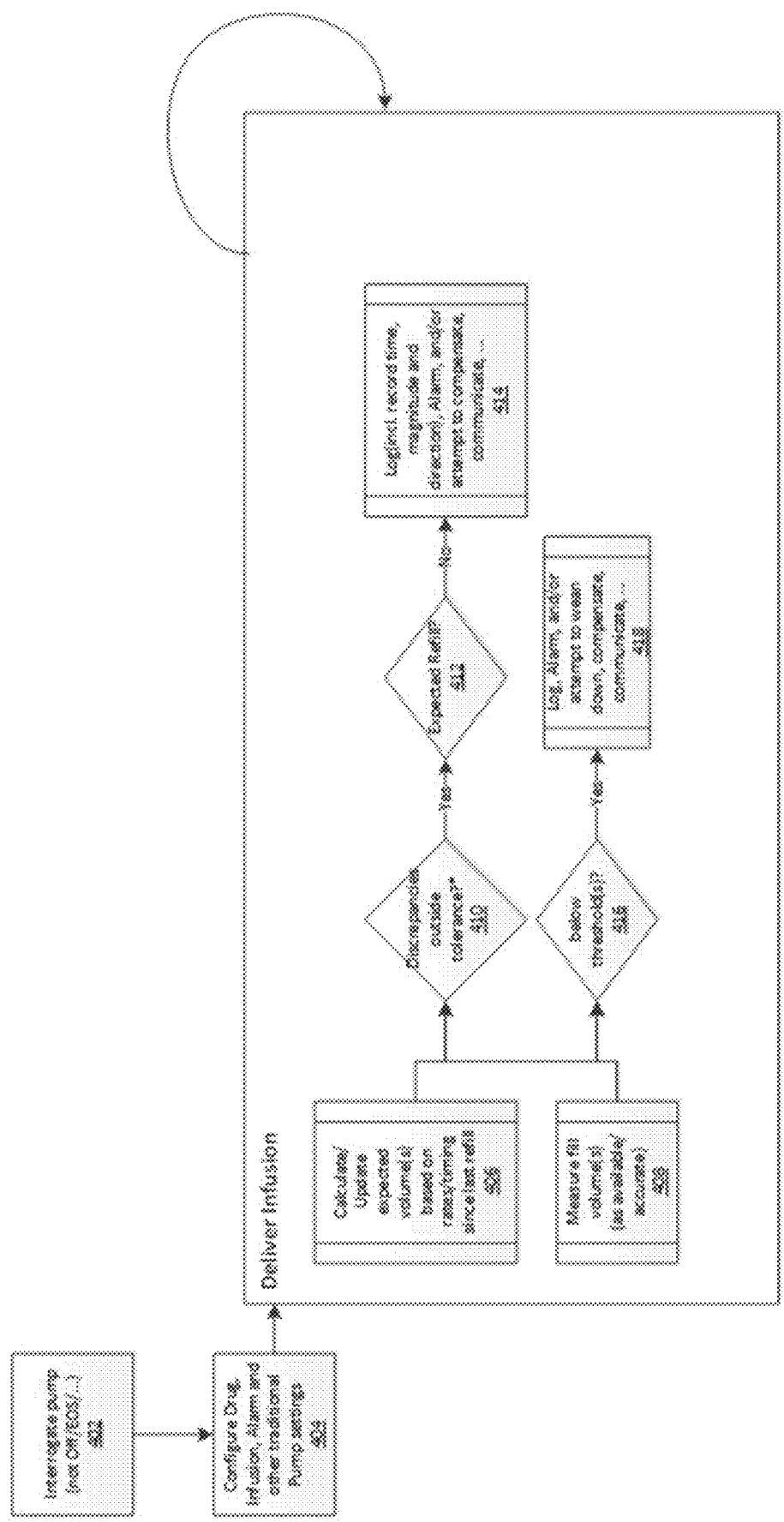
FIG. 9 depicts a flowchart modeling the comparison between an expected medicament volume and a measured medicament volume in accordance with an embodiment of the disclosure.

Some embodiments of the present disclosure can be utilized to measure discrepancies in medicament usage to update and refine windows for scheduling future refill procedures, by providing a comparison between an expected medicament volume and a measured medicament volume. Referring to FIG. 9, a flowchart modeling the comparison between an expected medicament volume and a measured medicament volume is depicted in accordance with an embodiment of the disclosure.

At 402, the external programmer 108 can interrogate the implantable medical pump 102, thereby establishing communication between the pump 102 and programmer 108, either directly or via server 110. At 404, the external programmer 108 can inquire as to whether it is desired to configure or update the pump settings. Thereafter, the pump 102 can commence or continue delivering medicament to a user.

At 406, either the pump 102 or programmer 108 can calculate or update an expected medicament volume based on the programmed pump parameters, which can include the infusion rate and timing since the last refill procedure. At 408, the quantity or volume of medicament within the medicament reservoir 116 can be measured directly, for example via fill sensor 139. The expected medicament volume can then be compared with the measured medicament volume. Any difference between the expected and measured medicament volume can then be compared to a predefined tolerance. If the difference in medicament volume exceeds the predefined tolerance, at 412, the medicament delivery system 100 can suggest one or more windows for scheduling of one or more future refill procedures. In one embodiment, the medicament delivery system 100 can further utilize predictive algorithms for estimating a medicament level within the medicament reservoir 116 and the approximate date or time in which a medicament low-level alert is likely to be triggered. In one embodiment, the logged data can be utilized to change the behavior of the medicament delivery system 100 between refills (e.g., increasing the duty cycle on particular sensors within the implantable medical pump 102). For example, in one embodiment, utilization of the needle detection sensor 138 or fill sensor 139 can be minimized between refill procedures, with an increase in utilization as the expected refill window is approached.

At 414, a pump rate of the medicament pump 118 can be adjusted to compensate for the difference in medicament volume. For example, if the measured volume exceeds the expected volume (e.g., under-infusion), the pump rate can be increased in proportion to the difference. Conversely, if the measured volume is less than the expected volume (e.g., over-infusion), the pump rate can be slowed in proportion to the difference. In some embodiments, the external programmer 108 can prompt a caregiver or user to manually adjust the pump rate of the medicament pump 118. In other embodiments, the pump rate of the medicament pump 118 can be automatically adjusted.

At 416, a determination can be made as to whether either the expected medicament volume or measured medicament volume is below a predefined threshold, thereby indicating a low volume of medicament within the reservoir 116. At 418, if the expected or measured medicament volume is below the predefined threshold, the medicament delivery system 100 can issue a medicament low-level alert configured to inform a caregiver or user about the low medicament volume. In some embodiments, the pump rate of the medicament pump 118 can be adjusted to compensate for the low medicament volume. For example, in one embodiment, the pump rate can be slowed, thereby prolonging the period of time over which the medicament can be delivered, as well as to decrease the likelihood of an occurrence of an abrupt clinical underdose.

In some embodiments, data sensed by the fill sensor 139 can be monitored during the refill procedure to ensure that the volume of medicament dispensed from the refilling apparatus 164 is entering the medicament reservoir 116, thereby providing an additional safeguard to inhibit the injection of medicament directly into the patient. The fill sensor 139 can further be utilized to execute top-offs and partial refills, where the reservoir 116 is not yet in need of a complete refill. In some embodiments, top-offs and partial refills can alleviate the need to aspirate the medicament reservoir 116 prior to refilling the medicament reservoir 116. In some embodiments, the fill sensor 139 can be utilized to improve the calculation of mixed medicament concentrations, or optimize bridge boluses.

In some embodiments, the fill sensor 139 can be utilized to provide an advance warning of insufficient medicament within the reservoir 116 prior to experiencing non-typical atmospheric pressure conditions. For example, in one embodiment, the medicament delivery system 100 can be configured to receive information from a caregiver or user that the patient intends to enter into a hyperbaric condition (e.g., scuba diving or a hyperbaric chamber). The fill sensor 139 can then be utilized to ensure that a sufficient quantity of medicament remains within the reservoir 116 to accommodate the expected pressure condition.

Proper positioning of the needle portion of a refilling apparatus 164 can further be confirmed through the use of a flexible diaphragm 140A-D having a nonlinear spring rate (such as that depicted in FIGS. 4A-D). In particular, a negative relative pressure within the medicament chamber 144 can create a spontaneous refill of a predefined volume of medicament upon proper insertion of a portion of the refilling apparatus 164 into the access port 132 (e.g., a flow of drug into the medicament chamber 144 without pressure applied to the refilling apparatus). Accordingly, when medicament within the medicament chamber 144 has been aspirated beyond the point where the compression spring rate of the flexible diaphragm 140 counteracts the pressure within the vapor chamber 146, the negative pressure created within the medicament chamber 144 can serve to spontaneously draw a predefined quantity of medicament into the medicament chamber 144. Introduction of additional medicament can be accomplished by applying pressure to the refilling syringe, after confirmation of the refilling apparatus 164 placement has been made via the spontaneous fill.

In some instances, the accuracy in determining a pressure within the medicament chamber 144 can decrease below a given medicament threshold, particularly when only a small quantity of medicament remains within the medicament chamber 144. In such instances, difficulties can arise in accurately determining the volume of medicament administered. Where the accuracy decreases below a prescribed standard, further pumping operations can be stopped, which can result in an abrupt clinical underdose. However, by increasing the compression spring rate as the flexible diaphragm 140 is compressed, such that a vacuum is created within the medicament chamber 144 relative to at least one of the atmospheric pressure or pressure within the vapor chamber 146, the flow rate from the medicament pump 118 can be reduced; thereby slowing the medicament flow rate such that the patient is able to use a larger volume of the stored medicament. Accordingly, in addition to promoting a spontaneous refill to inhibit the likelihood of an inadvertent pocket fill, embodiments of the present disclosure can further serve to minimize the unusable quantity of medicament within the reservoir 116 and prolong the period of time over which the medicament can be delivered, as well as to decrease the likelihood of an occurrence of an abrupt clinical under-dose.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A medicament delivery system configured to reduce the risk of inadvertently injecting medicament directly into a patient during a refill procedure via an external refilling apparatus, the medicament delivery system comprising:
an implantable medical pump including a refillable medicament reservoir accessible via an access port, wherein the refillable medicament reservoir includes a flexible diaphragm comprising a multi-stage biasing element having a nonlinear spring rate configured to create a relative vacuum within a medicament chamber when medicament is expelled from the medicament chamber beyond a predefined threshold, the multi-stage biasing element having a first biasing element and a second biasing element whereupon at least a partial compression of the first biasing element the flexible diaphragm transitions from a compression spring rate of the first biasing element alone to a higher, combined compression spring rate of both the first and second biasing elements, so as to spontaneously draw a quantity of medicament into the medicament chamber during the refill procedure to reestablish the predefined threshold, thereby confirming proper placement of a portion of the external refilling apparatus into the access port.

2. The medicament delivery system of claim 1, wherein the flexible diaphragm includes one or more convolutions configured to enable the flexible diaphragm to expand and contract between an expanded position and an empty position.

3. The medicament delivery system of claim 1, wherein the second biasing element has a higher compression spring rate than the compression spring rate of the first biasing element.

4. The medicament delivery system of claim 3, wherein the first biasing element and the second biasing element cooperate to naturally bias the flexible diaphragm towards an expanded position.

5. The medicament delivery system of claim 3, wherein as the flexible diaphragm contracts towards an empty position, the nonlinear spring rate of the flexible diaphragm transitions from the compression spring rate of the first biasing element to the higher compression spring rate of the second biasing element.

6. The medicament delivery system of claim 3, wherein the first biasing element includes one or more convolutions.

7. The medicament delivery system of claim 6, wherein the compression spring rate of the first biasing element is between 8-17 lbs/inch.

8. The medicament delivery system of claim 6, wherein the second biasing element includes at least one of: one or more convolutions having a higher compression spring rate than the first biasing element; a wave spring; a convex closed-end of the flexible diaphragm; a concave closed-end of the flexible diaphragm; or combination thereof.

9. The medicament delivery system of claim 1, wherein the medicament reservoir further includes a vapor chamber configured to apply a substantially constant pressure to an exterior portion of the medicament chamber.

10. The medicament delivery system of claim 9, wherein at the predefined threshold, the nonlinear spring rate of the flexible diaphragm reaches a magnitude sufficient to counteract the pressure applied by the vapor chamber.

11. The medicament delivery system of claim 10, wherein the predefined threshold is established when about 2 mL of medicament remains within the medicament chamber.

12. The medicament delivery system of claim 10, wherein further aspiration of medicament from the medicament chamber establishes a relative vacuum within the medicament chamber relative to the atmosphere.

13. The medicament delivery system of claim 1, further comprising a sensor configured to detect a presence of a portion of the refilling apparatus within the access port.

14. The medicament delivery system of claim 13, wherein data gathered by the sensor is logged for future use.

15. The medicament delivery system of claim 13, wherein data gathered by the sensor is utilized to prompt a programmer to display user feedback regarding placement of the portion of the refilling apparatus within the access port.

16. The medicament delivery system of claim 13, wherein data gathered by the sensor is utilized to prompt a programmer to display medicament refill information.

17. The medicament delivery system of claim 1, wherein the nonlinear spring rate is configured to prolong the period of time over which the medicament is delivered and decrease the likelihood of an occurrence of an abrupt clinical underdose.

18. A implantable medical pump configured to reduce the risk of inadvertently injecting medicament directly into a patient during a refill procedure via an external refilling apparatus, the implantable medical pump comprising:
a medicament reservoir configured to store a quantity of medicament, the medicament reservoir including a flexible diaphragm defining a medicament chamber; and
an access port configured to provide a pathway for medicament flowing into the medicament reservoir, wherein the flexible diaphragm comprises a multi-stage biasing element has a nonlinear spring rate configured to create a relative vacuum within the medicament chamber when medicament is expelled from the medicament chamber beyond a predefined threshold, the multi-stage biasing element having a first biasing element and a second biasing element whereupon at least a partial compression of the first biasing element the flexible diaphragm transitions from a compression spring rate of the first biasing element alone to a higher, combined compression spring rate of both the first and second biasing elements, so as to spontaneously draw a quantity of medicament into the medicament chamber during the refill procedure to reestablish the predefined threshold, thereby confirming proper placement of a portion of the external refilling apparatus into the access port.

19. The medicament delivery system of claim 18, wherein the nonlinear spring rate of the flexible diaphragm is established via a first biasing element and a second biasing element, wherein the second biasing element has a higher compression spring rate than the compression spring rate of the first biasing element.

20. A method of reducing the risk of inadvertently injecting medicament directly into a patient during a refill procedure of an implantable medical pump via an external refilling apparatus, the method comprising:
providing an implantable medical pump including a refillable medicament reservoir accessible via an access port, wherein the refillable medicament reservoir includes a flexible diaphragm comprises a multi-stage biasing element having a nonlinear spring rate configured to create a relative vacuum within the medicament chamber when medicament is expelled from the medicament chamber beyond a predefined threshold, the multi-stage biasing element having a first biasing element and a second biasing element whereupon at least a partial compression of the first biasing element the flexible diaphragm transitions from a compression spring rate of the first biasing element alone to a higher, combined compression spring rate of both the first and second biasing elements;
expelling medicament from the medicament chamber beyond a predefined threshold to establish a relative vacuum within the medicament chamber; and
inserting a portion of an external refilling apparatus into the access port of the implantable medical pump, wherein proper placement of the portion of the external refilling apparatus within the access port is confirmed by spontaneously drawing a quantity of medicament into the medicament chamber to reestablish the predefined threshold.

\* \* \* \* \*